(12) United States Patent
Juhl

(10) Patent No.: US 7,796,261 B2
(45) Date of Patent: Sep. 14, 2010

(54) SPECTROPHOTOMETER

(75) Inventor: Henrik Vilstrup Juhl, Roskilde (DK)

(73) Assignee: Foss Analytical A/S, Hillerod (DK)

( * ) Notice: Subject to any disclaimer, the term of this patent is extended or adjusted under 35 U.S.C. 154(b) by 354 days.

(21) Appl. No.: 11/792,097

(22) PCT Filed: Dec. 1, 2005

(86) PCT No.: PCT/EP2005/012820

§ 371 (c)(1), (2), (4) Date: Jun. 1, 2007

(87) PCT Pub. No.: WO2006/058741

PCT Pub. Date: Jun. 8, 2006

(65) Prior Publication Data

US 2008/0123094 A1 May 29, 2008

(30) Foreign Application Priority Data

Dec. 2, 2004 (DK) .............................. 2004 01883

(51) Int. Cl.
*G01N 21/00* (2006.01)

(52) U.S. Cl. ...................... 356/435; 356/246; 356/436; 356/440

(58) Field of Classification Search ................. 356/213, 356/218, 319, 409, 432, 440
See application file for complete search history.

(56) References Cited

U.S. PATENT DOCUMENTS 5,258,620 A  11/1993  Sueyasu et al.

(Continued)

FOREIGN PATENT DOCUMENTS

EP  0 145 877  6/1982
EP  0 145 877  6/1995
WO  WO 00/57158  9/2000

OTHER PUBLICATIONS

English translation of claims of DE 0145877 provided by EPO espacenet auto-translator (Oct. 10, 2007).

*Primary Examiner*—Traifur Chowdhury
*Assistant Examiner*—Tara S Pajoohi
(74) *Attorney, Agent, or Firm*—Harness, Dickey & Pierce, P.L.C.

(57) ABSTRACT

A spectrophotometer (2) comprising a source of radiation (6), preferably optical radiation, disposed to emit radiation at a plurality of wavelengths towards a sample in a sample holder (4) and a detection arrangement 8 for detecting the radiation after its interaction with the sample. The sample holder (4) is adapted to present a plurality of different path lengths for the emitted radiation through the sample. An arithmetic unit (10; 10b) is operably connected to receive an intensity dependent output from the detection arrangement (8) and is adapted to store an intensity value of the detected emitted radiation indexed to its wavelength at two or more path lengths of the plurality of different path lengths and to calculate a value dependent on the ratio of the indexed intensity values at each of two path lengths by which an indication of the presence of a substance of interest withiA spectrophotometer (2) comprise a source of radiation (6), preferably optical radiation, disposed to emit radiation at a plurality of wavelengths towards a sample in a sample holder (4) and a detection arrangement 8 for detecting the radiation after its interaction with the sample. The sample holder (4) is adapted to present a plurality of different path lengths for the emitted radiation through the sample. An arithmetic unit (10;10b) is operably connected to receive an intensity dependent output from the detection arrangement (8) and is adapted to store an intensity value of the detected emitted radiation indexed to its wavelength at two or more path lengths of the plurality of different path lengths and to calculate a value dependent on the ratio of the indexed intensity values at each of two path lengths by which an indication of the presence of a substance of interest within the retained sample can be obtained.

8 Claims, 2 Drawing Sheets

U.S. PATENT DOCUMENTS

Figure 1:
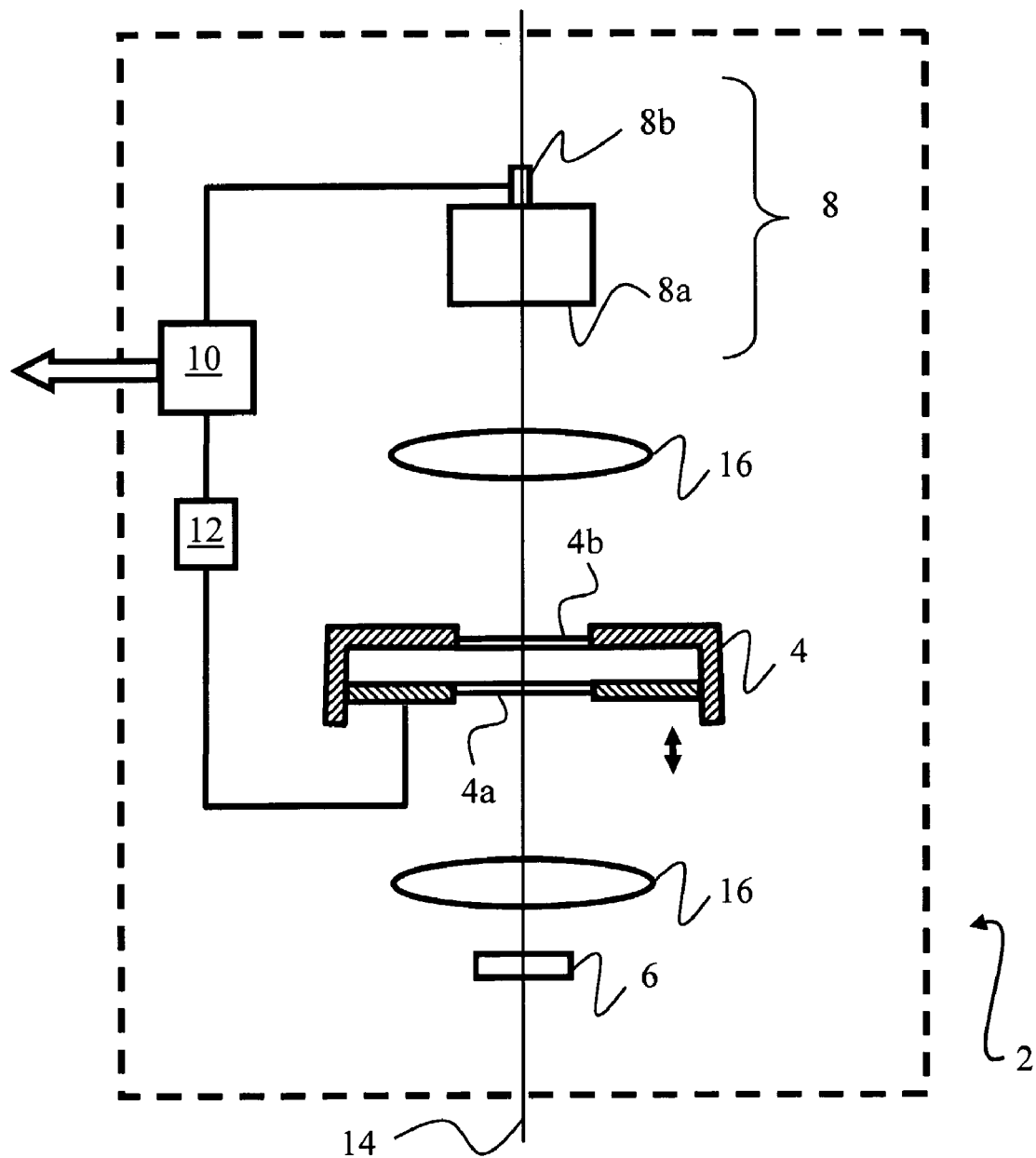

| | | |
|---|---|---|
| 5,371,020 A | 12/1994 | Frischauf |
| 5,453,619 A | 9/1995 | Asselain et al. |
| 5,602,647 A | 2/1997 | Xu et al. |
| 5,750,998 A | 5/1998 | Goldman |
| 5,963,335 A * | 10/1999 | Boutelle .................... 356/433 |

* cited by examiner

SPECTROPHOTOMETER

The present invention relates to a spectrophotometer.

It is well known to provide a spectrophotometer for the quantitative and/or qualitative determination of substances of interest in a test sample material, particularly a solution. Such a spectrophotometer detects electromagnetic energy, typically optical energy, at one or more defined wavelengths after its interaction with a test sample retained in a sample holder, such as a cell or cuvette. This spectrophotometer device may be configured to operate in one or more of the well known transmission, reflectance or transreflectance modes and may, for example, comprise a dispersion element monochromator or may, for example, be configured as an interferometer, such as a Fourier Transform interferometer.

It is also known from for example U.S. Pat. No. 5,602,647, the contents of which are incorporated herein by reference, to provide an optical spectrophotometer in which a sample holder has a variable internal optical path length. In this spectrophotometer the path length is varied in order to optimize the intensity of a particular wavelength detected. The spectrophotometer is configured to make the quantitative and/or qualitative determination based on the intensity of transmitted optical radiation and the values of the optical path length at peak intensity positions.

In known spectrophotometers random temporal intensity drift is a problem. This may be caused for example by unstable operating conditions such as variations in the temperature of the sample or the instrument; variations in the relative humidity of the surroundings; or variations in the detector sensitivity. As a solution to this problem it is well known to provide a so-called "zero-setting" of the spectrophotometer at regular operating intervals. During zero-setting a calibration sample, such as a water sample, is substituted for the test sample. The intensity of light reaching the detector after its interaction with the calibration sample ($I_{W\lambda}$) is monitored across the spectral region of interest. This intensity is then used to provide a wavelength dependent zero level across that spectral region. The intensity of light received after its interaction with a test sample ($I_{S\lambda}$) is then divided by the calibration sample light intensity ($I_{W\lambda}$) at the same wavelength ($\lambda$). In this manner an intensity related transmission value ($T_\lambda$) may be obtained in which all system effects are removed, these effects being considered as essentially the same for both the calibration sample and the test sample. This operation may be represented by the following equation to be solved within an arithmetic unit associated with the spectrophotometer:

$$T_\lambda = I_{S\lambda}/I_{W\lambda} \quad (1)$$

It will be appreciated that $T_\lambda$ can be considered as a measure of the deviation of the intensity of light from the test sample from that from the calibration sample.

This poses a problem that should a substance of interest within the test sample have an absorption band in regions where the calibration sample is strongly absorbent then the accuracy of any determination of the substance will be adversely affected.

A further problem is that in order to more accurately make a determination the path length for the radiation must be the same, to within a few tenths of micrometers, for both the calibration sample and for the test sample. This is difficult to achieve, particularly where the cuvette or cell holding the samples is constructed so that it can be opened for cleaning between sampling or where a different holder is used for the calibration sample and for the test sample.

Additionally, the zero-setting is only valid during the period where intensity drift is negligible. Thus either the zero-setting calibration must be carried out frequently, which is time consuming, or environmental stabilization elements must be provided in order to control one or both temperature and humidity within the spectrophotometer, which is expensive.

It is the aim of the present invention to alleviate at least some of the aforementioned problems and disadvantages.

Accordingly, a first aspect of the present invention provides a spectrophotometer as described in and characterized by the present Claim 1. By dividing the intensities of detected light of the same wavelength after they have traversed two different paths through the same sample then intensity related instabilities are removed. Zero-setting using a calibration sample can thus be simply and effectively avoided.

Advantageously, since test sample and calibration sample do not have to be interchanged in order to remove these instabilities the calculations unit may be configured to perform such ratio calculations at more regular intervals, preferably for each test sample, than would normally be acceptable to a user. In this way the time between effective zero-settings will be much less than the time constants normally associated with possible environmental variations and expensive stabilization elements may be omitted from the spectrometer device.

Moreover, by arranging for the calculations unit to perform said ratio calculations each time a new sample is introduced into the sample holder then any unplanned variations in optical path length through the sample, such as may occur with opening and closing of a cuvette to replace a sample or by dirt or other residue sticking to the inside of the holder, will be accommodated.

According to a second aspect of the present invention there is provided a method of determining by means of a spectrophotometer according to the first aspect of the present invention one or both a quantitative and a qualitative indication of a substance of interest within a test sample. Advantages associated with the spectrophotometer are thus inherent in the present method.

Figure 2:
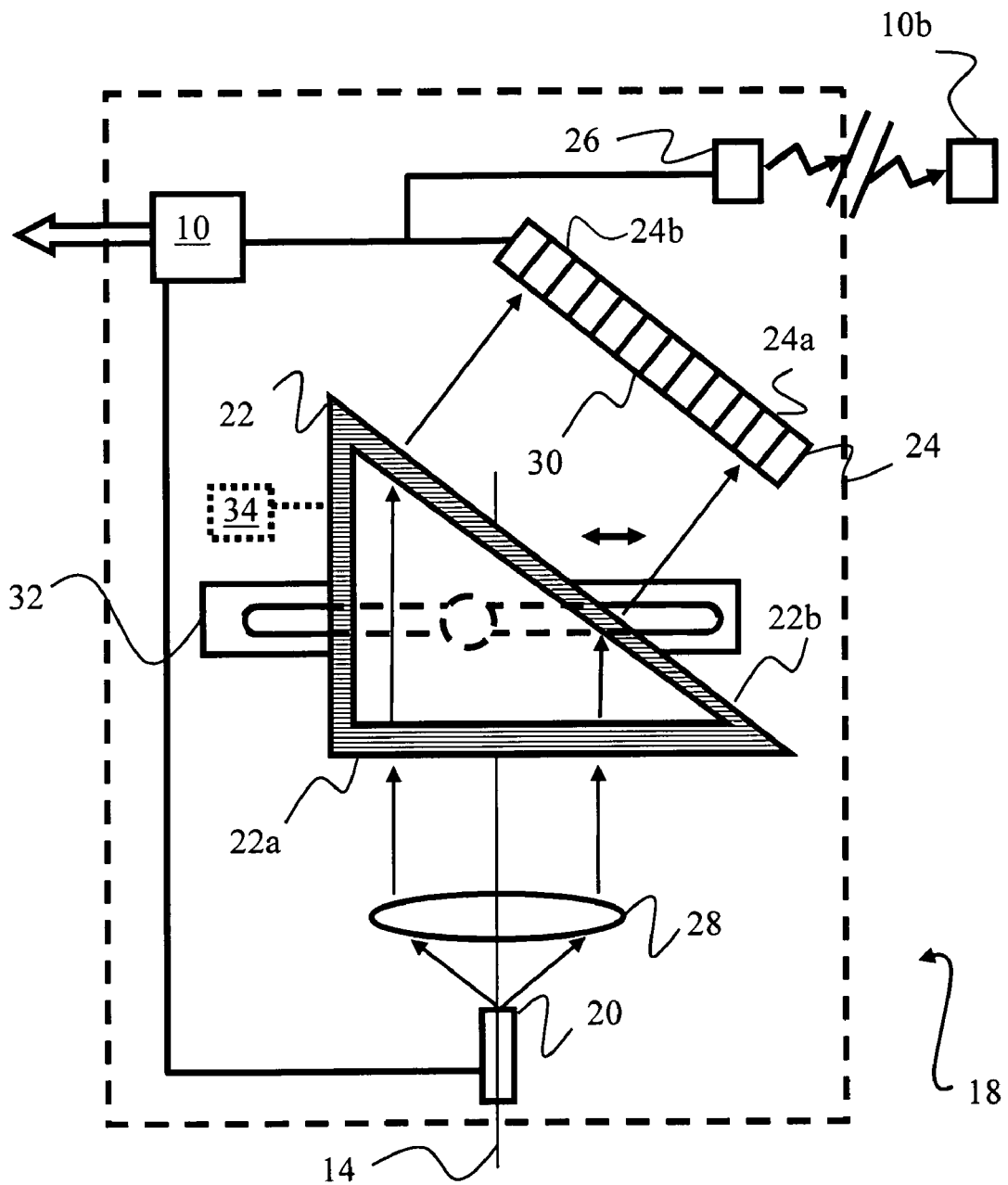

Embodiments of the present invention will now be described with reference to the drawings of the accompanying figures, of which:

FIG. 1 shows schematically a first embodiment of a spectrophotometer according to the present invention; and FIG. 2 shows schematically a second embodiment of a spectrophotometer according to the present invention.

Considering now a first exemplary embodiment of a spectrophotometer 2 shown in FIG. 1. The spectrophotometer 2 comprises a sample holder 4; a polychromatic light source 6, a detection arrangement 8; an arithmetic unit 10 and an actuator 12. In the present example the source 6, cell 4 and detection arrangement 8 are relatively disposed so that in use light from the source 6 passes along an optical axis 14 to be transmitted through opposing surfaces 4a, 4b of the cell 4 before being detected by the detection arrangement 8. Focussing optics 16, here shown as a pair of lenses, may be provided and employed in a known manner to form the desired light beam shape from the source 6, through the sample holder 4 and to the detection arrangement 8.

The sample holder 4 of the present embodiment is configured with the opposing surfaces 4a, 4b in a direction along the optical axis 14 formed in whole or in part of light transmitting material and being movable relative to one another. The actuator 12 is operably connected to one or both opposing faces 4a, 4b in order to exert a force thereon so as to change their relative separation (illustrated in the Figure by the double-headed arrow) and hence the optical path length through the sample cell 4.

The polychromatic light source 6 is here configured to generate and emit all of the specific wavelengths of interest simultaneously. To complement this the detection arrangement 8 is here comprised of a spectrometer 8a and an associated photo-detector 8b. These elements 8a, 8b are mutually configured in a known manner so as to be able to generate a wavelength dependent transmission spectrum of sample material within the sample cell 4.

The arithmetic unit 10 is operably connected to an output of the photo-detector 8b and, in the present example, also to the actuator 12. The arithmetic unit 10 is configured to receive and preferably to store a so generated transmission spectrum at a plurality, being preferably least two, different separations of the two faces 4a, 4b. The unit 10 may be configured to store both the spectra as well as the corresponding separation as indicated by an output from the actuator 12 and may comprise a plurality of separate but interconnected units rather than the single functional unit 10 that is illustrated in the present embodiment.

In operation the arithmetic unit 10 of the present embodiment records spectral data from the detection arrangement 8 corresponding to a first separation of the cell walls 4a, 4b. The actuator 12 is then operated to change the separation between the cell walls 4a, 4b and the arithmetic unit 10 records spectral data from the detection arrangement 8 corresponding to a second, different, separation of the cell walls 4a, 4b. In this manner intensity values for light from the polychromatic source 6 which is transmitted through the sample material, indexed to their wavelengths, are available to the arithmetic unit 10 for at least two different optical paths through the sample material. The arithmetic unit 10 is configured to make a quantitative or a qualitative determination of the presence of a substance of interest within the sample material based on calculations of the ratio of the thus obtained intensity values at the same wavelengths for each of the two different path lengths. The unit 10 is further configured to then output an indication of the so made determination. This may, for example, be in the form of a quantitative measure of the substance of interest or may be, for example a qualitative indication of the presence of the substance of interest within the sample.

More specifically the calculations unit 10 is configured to make use of methodology encapsulated by the following equations when carrying out the determinations:

The intensity of light of wavelength $\lambda$, ($I_{1\lambda}$) that is received at the detector 8b after traversing a path length $b_1$ through a sample having an absorption coefficient $a_\lambda$ (includes both sample and holder absorption coefficients) and containing a concentration, C, of a substance of interest may be expressed according to the known equation:

$$I_{1\lambda} = I_{0\lambda} \exp(a_\lambda \cdot C \cdot b_1) \quad (2)$$

where $I_{0\lambda}$ is the intensity of the light of wavelength $\lambda$ incident at the face 4a of the holder 4.

Similarly for a shorter path length $b_2$ the intensity received by the detector 8b at the same wavelength $\lambda$ may be expressed as:

$$I_{2\lambda} = I_{0\lambda} \exp(a_\lambda \cdot C \cdot b_2) \quad (3)$$

Remembering equation (1) then the zero-setting of the sample (now effectively relative to air) may be expressed as:

$$T_\lambda = I_{1\lambda}/I_{2\lambda} \quad (4)$$

Or a wavelength dependent absorbance $A_\lambda$ may be expressed as:

$$A_\lambda = \log(I_{2\lambda}/I_{1\lambda}) = a_\lambda \cdot C \cdot (b_1 - b_2) \quad (5)$$

Thus in a most simple configuration the arithmetic unit 10 may be configured to determine the concentration C from equation (5) and from a knowledge of the two path lengths $b_1$ and $b_2$ (at least their difference); the associated detected intensities $I_{1\lambda}$ and $I_{2\lambda}$ and the value of the absorption coefficient $a_\lambda$ at the wavelength(s), $\lambda$, of interest.

However, more commonly, the science of chemometrics may be applied to the problem in a generally known manner whereby multivariate statistical analysis is employed in order to produce a calibration algorithm which establishes a correlation of the absorbance, $A_\lambda$, to the concentration, C, of a substance of interest. As is well known, this involves the use of a set of "training" or calibration samples which are preferably selected to span the complete range of concentrations and substances likely to be of interest. New to the present invention, spectra are acquired for each calibration sample in turn where the likely optical path differences ($b_1 - b_2$) are also spanned. From these spectra a calibration equation or algorithm is established that links the optical path length dependent spectroscopic data by wavelength and the quantified presence of the substance(s) of interest. It will be appreciated that in this manner the actual optical path or path difference for any test sample need not be known in order for the arithmetic unit 10 to make a prediction regarding a particular one or more substances of interest.

FIG. 2 shows a second embodiment of a spectrophotometer 18 according to the present invention. Here a polychromatic light source 20 is tuneable in a known manner to serially emit light of specific wavelengths of interest along an optical axis 14 and towards a sample holder 22. The light source 20 may, for example, comprise a known laser diode arrangement that is tuneable to output a known wavelength or may include a dispersion element (such as in a grating monochromator) or a filter element which is adjustable to select for emission a known wavelength from a polychromatic incident light beam.

A detection arrangement 24 is disposed to collect light from the source 20 after its transmission through sample material within the sample holder 22. The detection arrangement 24 is configured to provide an output to an arithmetic unit 10 that is indicative of the intensity of the collected light.

Additionally or alternatively, the output may be provided to a transmitter unit 26 for the onward transmission, for example via the Internet or other communications network, to an arithmetic unit 10b that is located external the spectrophotometer 18, for example at a remote central facility, and which may be capable of processing information from a plurality of connected similar spectrophotometers. It will be appreciated that the arithmetic unit 10b may simply be an element of a standard personal computer located in close proximity to the spectrophotometer 18 and also that transmission may be via a wire link.

The sample holder 22 is, in the present example, comprised of a transparent cell of right-angled triangular cross-section and is disposed to provide a plurality of different optical paths dependent on the position at which the light emitted from the source 20 is incident on a first face 22a of the cell 22. Optics 28 are provided in the present embodiment in order to generate a collimated light beam at the first face 22a of the cell 22 having a much larger cross sectional area than that of the beam originally emitted by the source 20.

The detection arrangement 24 comprises a detection surface 30 that is disposed parallel to a second face 22b, being the hypotenuse, of the cell 22 through which light is transmitted after its interaction with the sample material retained within cell 22. With this arrangement the optical path traveled by the light outside the cell 22 is the same irrespective of where on the detection surface 30 it is detected. The detection surface 30 is, in the present embodiment, adapted to generate differentiable position sensitive intensity signals and may for example comprise linear array of two or more separate detection elements 24a, 24b. With this configuration the output from the detection arrangement 24 can advantageously provide to the arithmetic unit 10 (and possibly 10b) values for the intensity of light from a plurality (here two) optical path lengths simultaneously and in a differentiable manner.

The arithmetic unit 10 (and possibly 10b) receives the output from the detection arrangement 24 and, in the present embodiment, an output from the source 20 indicating the emission wavelength, $\lambda$, and is in this manner provided with access to wavelength indexed intensity values for at least two different path lengths simultaneously. These values may be stored for later processing or may be processed in real time in a manner described above with respect to the operation of the arithmetic unit 10 of FIG. 1 in order to provide, in accordance with the equations above, an output indicative of the presence of a substance of interest within the sample in the cell 22.

In embodiments where there are provided more than two detection elements 24a,b, . . . then the arithmetic unit 10,10b may be advantageously configured to derive a plurality of values indicative of the substance of interest in a same sample from intensity values obtained at different pairs of path lengths (corresponding to different pairs of detection elements 24a,b, . . . ) and using equation (5) above. These so derived plurality of values may be simply combined to provide an average value quantitatively indicating the presence of the substance of interest or may be combined, such as by appropriately weighting each value, in order to provide such a quantitative indication.

It will be appreciated that embodiments according to FIG. 1 may also be configured to provide such multiple indications simply by configuring the actuator 12 to operate in a manner so as to provide three or more different separations of the two faces 4a,4b at which spectra are to be recorded and stored by the arithmetic unit 10.

In an alternative configuration of the spectrophotometer 18 of FIG. 2 the cell 22 is mounted on a support 32 for translation in a plane perpendicular to the direction of travel of the incident light beam (that is, along the optical axis 14). This translation is indicated by the double-headed arrow in the figure. An actuator 34 (broken line construction) such as a screw actuator, is operably connected to translate the cell 22. This configuration is such that translation of the cell 22 relative to the beam emitted by the light source 20 causes different optical path lengths through the cell 22 to be serially presented to a same point in the incident beam. The collimating lens 28 may be omitted and the detection arrangement 24 need not be constructed to provide differentiable position sensitive intensity signals. Of course an analogous effect may be achieved by appropriate translation of either or both the light source 20 and the detection arrangement 24 either in conjunction with or as an alternative to the translation of the cell 22.

It will be appreciated by those skilled in the art that the sample holder 4;22 may be incorporated into other spectrophotometer arrangements, such as into an optical path of an arm of a known Fourier Transform Infra-red (FTIR) spectrophotometer arrangement, without departing from the invention as claimed.

It will be further appreciated that radiation in wavelength regions other than the optical wavelength regions (Ultraviolet through Infra-red) may be employed, always provided that its interaction with a test sample may be described by the equations (1)-(5) above.

The invention claimed is:

1. A spectrophotometer comprising:
 a sample holder adapted to present internally a plurality of different path lengths to radiation of one or more wavelengths emitted from a source;
 a detection arrangement for detecting a wavelength dependent intensity of emitted radiation after traversing one of the plurality of different path lengths and for providing an output indicative thereof; and
 an arithmetic unit operably connected to receive the output and to generate therefrom at least one or both a quantitative and a qualitative indication of a substance of interest within a sample,
 wherein the arithmetic unit calculates a value according to a division of received outputs for a same one of one or more emitted wavelengths at two different path lengths of the plurality of different path lengths so as to remove intensity instability and to generate therefrom the at least one of the quantitative and qualitative indications.

2. A spectrophotometer as claimed in claim 1, wherein the sample holder comprises a cell provided with two opposing faces relatively movable so as to provide the plurality of path lengths and further comprises an actuator co-operable with the cell to exert a force thereon for effecting relative movement of the two opposing faces.

3. A spectrophotometer as claimed in claim 1, wherein the sample holder is provided with two opposing faces, at least one of which forms an oblique angle to an axis being parallel to a direction of travel for the emitted radiation.

4. A spectrophotometer as claimed in claim 3, further comprising an actuator operably coupled to the sample holder to effect its translation in a direction perpendicular to the axis.

5. A spectrophotometer as claimed in claim 1, wherein the sample holder and the detection arrangement are mutually configured in a transmission spectrophotometric arrangement.

6. A method of determining by means of a spectrophotometer of at least one of a quantitative indication and a qualitative indication of a substance of interest within a test sample, said method comprising:
 a) recording at each of one or more wavelengths and using the spectrophotometer an intensity value of radiation having traversed a first path length within the sample; and
 b) repeating at least once the step a) for radiation at each of the one or more wavelengths having traversed a further, different, path length within the sample;
 c) calculating in an arithmetic unit a value dependent on the ratio of the intensity values recorded at each of two path lengths for a same each of one or more wavelengths; and
 d) determining in the arithmetic unit the indication of the substance based on the one or more values calculated at step c).

7. A method according to claim 6, wherein
 step b) is repeated a plurality of times, each at a different further optical path length within the sample; and
 step c) is repeated a plurality of times wherein each time a value is calculated using a different two of the plurality of path lengths employed in step b).

8. A method according to claim 6, wherein the determination of the indication comprises calculating a concentration of substance of interest by applying calibration parameters established by multivariate analysis.

* * * * *